United States Patent [19]

Koparkar et al.

[11] Patent Number: 5,284,662
[45] Date of Patent: Feb. 8, 1994

[54] ORAL OSMOTIC SYSTEM FOR SLIGHTLY SOLUBLE ACTIVE AGENTS

[75] Inventors: Arun D. Koparkar, Westfield; Shailesh B. Shah, Union, both of N.J.

[73] Assignee: Ciba-Geigy Corp., Ardsley, N.Y.

[21] Appl. No.: 809,026

[22] Filed: Dec. 16, 1991

Related U.S. Application Data

[63] Continuation of Ser. No. 590,880, Oct. 1, 1990, abandoned.

[51] Int. Cl.$^5$ .............................................. A61K 9/24
[52] U.S. Cl. ..................................... 424/473; 424/465
[58] Field of Search ............... 424/473, 484, 485, 486, 424/488, 469

[56] References Cited

U.S. PATENT DOCUMENTS 4,857,336  8/1989  Khanna et al. ...................... 424/484

*Primary Examiner*—Thurman K. Page
*Assistant Examiner*—Leon R. Horne
*Attorney, Agent, or Firm*—Irving M. Fishman; Karen G. Kaiser; Barbara J. Ikeler

[57] ABSTRACT

An oral sustained release composition for slightly soluble pharmaceutically active agents comprising a core, a wall around said core, and a bore through said wall connecting said core and the environment outside of said wall; wherein said core comprises a slightly soluble active agent, optionally a crystal habit modifier, at least two osmotic driving agents, at least two different (or two different grades of) hydroxyalkyl celluloses, and optionally lubricants, wetting agents, and carriers; said wall being substantially impermeable to said core components and permeable to water and gastro-intestinal fluids. The composition is most especially adapted for administering carbamazepine.

23 Claims, No Drawings

ORAL OSMOTIC SYSTEM FOR SLIGHTLY SOLUBLE ACTIVE AGENTS

This application is a continuation of application Ser. No. 590,880, filed Oct. 1, 1990, now abandoned

FIELD OF THE INVENTION

The invention relates to the field of oral osmotic active agent dispensers, and particularly to such dispensers especially adapted for slightly soluble active agents. The invention relates particularly to such dispensing systems for carbamazepine.

BACKGROUND OF THE INVENTION

Oral osmotic systems have been known in the art for some time, being initially developed by Alza Corp. in the late 1970's. Since then there have been a number of variations on the general theme reported in both the patent and scientific literature. Of special significance to the present invention is U.S. Pat. No. 4,857,336 ('336), issued to Khanna on Aug. 15, 1989, which is incorporated in toto herein by reference. This patent discloses carbamazepine oral osmotic systems having a core of carbamazepine, hydroxypropylmethyl cellulose as a crystal habit modifier for carbamazepine, mannitol as an osmotic driving agent, two different grades of hydroxyethyl cellulose (in a 1:1 weight ratio) as the core matrix polymers, lubricant and wetting agent; and a semipermeable wall with a bore connecting the core and the outer environment. The present invention is an improvement of the '336 invention with respect to carbamazepine and other slightly soluble agents. While the '336 disclosed examples can be prepared to deliver reasonable carbamazepine amounts over time in the desired fashion, the instant invention possesses a number of distinct advantages.

First, other '336 formulations than that described above require a two step manufacturing process utilizing two organic solvents to prepare the core. From a manufacturing cost and environmental standpoint, it would be highly desirable to reduce the processing steps and avoid the use of organic solvents as much as possible.

Secondly, with those other core formulations, end point detection in the granulation steps is difficult resulting in insufficient or excess solvents being used. Excessive solvent in the granulation results in an unsuitable pasty mass rather than a granulation acceptable for compression into cores.

While Example 4 of '336 has been found to be processable in a single granulation step, avoiding the cost disadvantages, and resulting in reducing the amount of organic solvent use, that formulation does not deliver carbamazepine as desired.

OBJECTS OF THE INVENTION

It is an object of the invention to further reduce the use of organic solvent in preparing oral osmotic dosage forms, particularly in the core, of slightly soluble drugs.

It is another object of the invention to provide an oral osmotic dosage form for slightly soluble agents which is more easily processable than the known '336 formulations.

It is yet another object of the invention to provide an oral osmotic dosage form for slightly soluble active agents providing approximately zero-order release of active agent while still achieving the objects set forth above.

SUMMARY OF THE INVENTION

Surprisingly, these and other objects have been achieved by an oral osmotic dosage form comprising a core comprising a pharmaceutically effective amount of a slightly soluble pharmaceutically active agent; optionally a crystal habit modifying agent for said active agent; at least two different grades of a hydroxy($C_1$-$C_4$)alkyl cellulose or two different hydroxy($C_1$-$C_4$)alkyl celluloses; a $C_6$ sugar alcohol; a mono or disaccharide; optionally a lubricant; and optionally a wetting agent;

a semipermeable wall allowing the passage of water but impermeable to the core cellulosic components, the core sugar alcohol, the core mono and disaccharides, and the active agent; and a hole through the wall connecting the core with the environment external to the wall, through which core components are delivered to the external environment once the dosage form is wetted.

DETAILED DESCRIPTION OF THE INVENTION

An oral osmotic dosage form for controlled release of a slightly soluble pharmaceutically active agent comprising (a) a core comprising
  (i) a slightly soluble pharmaceutically active agent in an amount sufficient to deliver a pharmaceutically effective amount thereof for the designed delivery time;
  (ii) optionally an effective amount of a crystal habit modifier for said active agent;
  (iii) at least two different hydroxy-$C_1$-$C_4$alkyl celluloses which may be hydroxyalkyl celluloses having different alkyl groups or hydroxyalkyl celluloses having the same alkyl group but the hydroxyalkyl cellulose being of differing grades;
  (iv) a $C_6$ sugar alcohol;
  (v) a mono- or di-saccharide;
  (vi) optionally an effective amount of a tabletting lubricant; and
  (vii) optionally an effective amount of wetting agents; and (b) a semipermeable wall around said core permeable to water of gastrointestinal fluid; and (c) a hole through said semipermeable wall connecting said core with the external environment.

Active agents with solubilities in the range of from about 0.05 mg/ml to about 60 . mg/ml in water at 20° C. are suitable, although actives with even greater solubilities may be used. In addition those actives having solubilities of less than 0.05 mg/ml in water at 20° C. may be used if their potencies are high enough so that an effective amount is suitably delivered notwithstanding the low solubility.

Non-pharmaceutical active agents which can be dispensed can be dispensed via the present invention include, but are not limited to:

(a) biologically active materials, such as veterinary products, and agricultural chemicals;
(b) general chemicals such as sealants, lubricants, etc.;
(c) catalytic agents for use in aqueous systems;
(d) monomers for polymerization in aqueous systems; and
(e) various diagnostic agents.

Typical pharmaceutical agents which may be administered via the instant invention include, but are not limited to:

(a) Central Nervous System agents such as: antipsychotics, anticonvulsants including carbamazepine, and oxcarbazepine, antidepressants, antiepileptics, anxiolytics, and hypnotics;

(b) cardiovascular agents such as:

anti-arrhythmics, hypolipedemics, anti-anginals, anticoagulants, anti-hypertensives, antiplatelets, diuretics, and electrolytes (Ca, K, Mg); and (c) antiinflammatories, antiasthmatics, antiarthritics, oral hypoglycemics, and aromatase inhibitors; to name a few.

The active drug that can be delivered includes inorganic and organic compounds without limitation, including drugs that act on the peripheral nerves, adrenergic receptors, cholinergic receptors, nervous system, skeletal muscles, cardiovascular, smooth muscles, blood circulatory system, synaptic sites, neuroeffector junctional sites, endocrine and hormone systems, immunological system, reproductive system, skeletal system, alimentary and excretory systems, inhibitory of hormonal and histamine systems, those materials that act on the central nervous system such as antidepressants, including amiflamine, amitriptyline, alaproclate, protriptyline, doxepin, imiprimine, trazodone, paprotiline, zimelidine, fluvoxamine; antipsychotic-neuroleptic agents such as chlorpromazine, haloperidol, thioridazine, trifluoperazine, MK-0212, remoxipride; anticonvulsants such as carbamazepine, oxcarbamazepine, phenytoin, phenobarbital; sedative-hypnotic agents such as triazolam, chlordiazepoxide, temazepam, chlorazepate, alprazolam, diazepam, flurazepam, lorazepam, oxazepam, hydroxyzine, prazepam, meprobamate, butalbital, orphenadrine, chlorzoxazone, cyclobenzaprine; antiparkinson agents such as benztropine, carbidopa, levodopa, L 647,339; analgesics such as acetaminophen, oxycodone, hydrocodone, codeine, propoxyphen. Respiratory agents including sympathomimetics, brochodilators, antihistamines, and antiasthmatics such as diethylpropion, ephedrine, epinephrine, isoproterenol, metaproterenol, terbutaline, cyproheptadine, azatadine, diphenhydramine, promethazine, chlorpheniramine, brompheniramine, aminophylline, theophylline, albuterol, tranilast, enprofylline, budesonide may also be used. Cardiovascular and antihypertensive agents including coronary vasodilators, cardiac glycosides, beta-blockers, slow calcium channel blockers, antiarrhythmics, peripheral vasodilators such as isosorbide dinitrate, nitroglycerin, dipyridamole, digoxin, nadolol, propranolol, metaprolol, atenolol, timolol, disopyramide, procainamide, nifedipine, quinidine, lidocaine, diltiazam, verapamil, prazosin, clonidine, hydralazine, methyldopa, captopril, metyresine, enalapril, lysinopril, felodipine, tocainide may also be used. Diuretics such as amiloride, spiranolactone, hydrochlorothiazide, chlorothiazide, acetazolamide, chlorthalidone, metolazone, furosemide, triamterene, methyclothiazide, ethacrynic acid, indacrinone; antiartereosclerotic agents such as mavinolin; hormones and steroids including estrogens such as conjugated estrogens, estradiol, ethinyl estradiol, diethylstilbesterol; progestins such as progesterone, hydroxyprogesterone, medroxyprogesterone, norethindrone; glucocorticoids and mineralocorticoids such as hydrocortisone, betamethasone, dexamethasone, methylprednisolone, prednisolone, prednisone, triamcinolone, and MK-0621 may also be used. Nonsteroidal anti-inflammatory agents, antiarthritic and antigout agents such as allopurinol, aspirin, fenprofen, ibuprofen, indomethacin, naproxen, phenylbutazone, sulindac, tolmetin, diflunisol, piroxicam, meclofenamate, penicillamine, probenecid, and colchicine; gastrointestinal agents including anticholinergics, antispasmodics, antidiarrheal, and antiulcer histamine-$H_2$-antagonists such as bethanechol, clidinium, dicyclomine, meclizine, prochlorperazine, trimethobenzamide, loperamide, cimetadine, ranitidine, diphenoxylate, famotidine, and omeprazole; oral hypoglycemics such as chlorpropamide, tolazamide, and tolbutamide; anticoagulants such as warfarin, phenindione, and anisindione; anti-infective agents including antibiotic, antimicrobial, antiviral, antiparasitic, and antifungal agents such as cefoxitin, thiabendazole, cephalexin, tetracycline, ampicillin, amoxicillin, sulfamethoxazole, cefaclor, erythromycin, penicillin, nitrofurantoin, minocycline, doxycycline, cefadroxil, miconazole, phenazopyridine, norfloxacin, clorsulon, fludalanine, pentizidone, cilastin, phosphonomycin, ivermectin, imipenem, arprinocid, and foscarnet; nutritional supplements including vitamins such as isotretinoin (Vit. A), Vit. D, tocopherols (Vit. E), and phytonadione (Vit. K); amino acids such as L-tryptophan and L-lysine; and lipids such as corn oil and medium chain triglycerides may also be used.

The drug can be prepared in various forms to be suitable for use herein such as esters of acids or alcohols and amides. Also a drug that is water soluble can be chemically modified to make it less water soluble and more lipid soluble. Such drugs or complexes can be delivered from the device and can be converted by enzymes, hydrolyzed by body fluids or other metabolic processes to a biologically active form. The agent can be in the core as a solution, dispersion, particle or powder. Generally, the device can house from 1 μg to 5 grams or more, with individual devices containing for example 1 μg, 1 mg, 5 mg, 500 mg, 1 g and the like. However, any beneficially or pharmacologically active amount is sufficient in the case of drugs.

The crystal habit modifying agent is necessary only when the active agent exists in more than one crystal form and the desired form to administer is not the most stable form so that crystal modification and resulting changes in solubility and other properties occur. Even so, the crystal habit modifying agent is only necessary when the resultant property change is sufficiently large to be of concern. The property most indicative of the need for a crystal habit modifying agent is solubility. If the solubility of the desired form for administration (Sd) differs from the form into which the active agent would change in the absence of the modifying agent (Su) by a value of X as defined in equation 1, the modifying agent is necessary.

$$(100\%) \left[ \frac{|Sd - Su|}{(\text{smaller of } Sd \text{ or } Su)} \right] \geq X \quad (1)$$

where 'X' is about 33% or less the crystal habit modifying agent is useful but not absolutely necessary; when 'X' is 40%, the modifying agent is necessary; when 'X' is 60%, the modifying agent is important; and when 'X' is 90% it is highly important.

A few examples of compounds that have crystal habit problems include carbamazepine and the xanthenes, such as aminophylline, theophylline, and to some extent caffeine.

Particularly suitable crystal habit modifying agents are dispersible cellulose ether, e.g. alkylated cellulose such as methyl or ethyl cellulose, hydroxypropyl cellulose, hydroxypropyl alkyl cellulose, e.g. hydroxypropyl methyl- or ethyl cellulose, carboxymethyl cellulose in salt form, e.g. sodium carboxymethyl cellulose, or carboxymethyl alkyl cellulose in salt form, e.g. sodium carboxymethyl methyl cellulose or sodium carboxymethyl ethyl cellulose, and gelatin, preferably type A gelatin.

The most suitable crystal habit modifying agents are methylated cellulose esters, e.g. methyl cellulose having a methoxy content of c. 27.0 to 32.0% and a degree of substitution of c. 1.75 to 2.1, or hydroxypropyl methyl cellulose having a methoxy content of c. 16.0 to 30% and a hydroxypropoxy content of 4.0 to 12.0%. The delivery system of this invention, when it contains crystal habit modifiers such as hydroxypropyl methyl cellulose, contains them in a preferred amount by weight of about 0.5 to about 15%, preferably about 1% to about 14%, more preferably about 2.5% to about 13%, still more preferably about 14% to about 10%, yet more preferably 4% to about 7%, most preferably about 5%—about 6% based on the amount of active agent.

The hydroxyC$_1$-C$_4$alkyl cellulose in the core preferably is of two different types, selected from those having different alkyl group and those of different grades but having the same alkyl group. For example, a combination of hydroxymethyl cellulose with hydroxyethyl cellulose is suitable. Also suitable is a combination of hydroxyethyl cellulose 250 H and hydroxyethyl cellulose 250 L. In these designations, the "250" indicates the degree of substitution and the "L" and "H" refer to the viscosity and thereby the molecular weight. The hydroxyethyl celluloses are typically available under the name Natrosol ® (from Hercules) or Cellosize ® (from Union Carbide) or Tylose ® (from Hoechst Celanese).

Additional polymers which may be used in combination with the foregoing hydroxyC$_1$-C$_4$alkyl cellulose combination include water-soluble aliphatic or cyclic poly-N-vinyl-amides, e.g. poly-N-vinylmethylacetamide, poly-N-vinylethylacetamide, poly-N-vinylmethylpropionamide, poly-N-vinylethylpropionamide, poly-N-vinylmethylisoubutyramide, poly-N-vinyl-2-pyrrolidone, poly-N-vinyl-2-piperidone, poly-N-vinyl-ε-caprolactam, poly-N-vinyl-5-methyl-2-pyrrolidone or poly-N-vinyl-3-methyl-2-pyrrolidone, preferably poly-N-vinylpyrrolidone having an average molecular weight of c. 10,000 to 360,000, swellable polyvinyl acetate or polyvinyl alcohol having a different acetate or residual acetate content, e.g. polyvinyl alcohol having a molecular weight of c. 5000 to 400,000, or polyvinyl acetate having a degree of hydrolysis of c. 85-98% and a degree of polymerization of c. 500 to 2500, alkylene oxide homopolymers, e.g. polypropylene oxide, preferably ethylene oxide homopolymers, having a degree of polymerization of c. 2000 to 100,000 and known e.g. under the registered trademark Polyox ® (Union Carbide); homopolymers such as polyhydroxy alkylmethacrylate having a molecular weight of 5000 to 500,000, anionic or cationic hydrogels, mixtures of agar and carboxymethyl cellulose, swellable agents consisting of methyl cellulose in admixture with lightly crosslinked agar, water-swellable polymers which can be obtained by dispersing the finely particulate copolymer of maleic anhydride and styrene, as well as polyalkylenes, e.g. polyethylene, polypropylene or polyisobutylene.

A particularly preferred combination of hydroxyC$_1$-C$_4$alkyl celluloses is hydroxyethyl cellulose 250 H with hydroxyethyl cellulose 250 L. With particular reference to this combination, the weight ratio of the 250 H to 250 L is advantageously about 1:4 to 4:1, preferably about 1:3 to about 3:1, more preferably about 1:2 to about 2:1, most preferably about 2:1.

In general, the hydroxy C$_1$-C$_4$ alkyl cellulose is present in an amount of about 2% to about 15%, preferably about 3% to about 12.5%, most preferably about 5% to about 6% by weight based on the total core weight.

The C$_6$ sugar alcohol is typically selected from mannitol, sorbitol, galactilol, inositol, and xylitol, most preferably mannitol.

The mono- or di-saccharide is typically selected from glyceraldehyde, threose, erythrose, lyxose, xylose, arabinose, ribose, talose, galactose, idose, gulose, mannose, glucose, altrose, xylulose, tagatose, sorbose, psicose, hamamalose, allose, their corresponding ketoses and deoxy forms, sedoheptulose, maltose, lactose, sucrose, cellobiose, isomaltose, and mixtures thereof, especially dextrates, N.F.

The combined weight of the C$_6$ sugar alcohol and the mono- or di-saccharide comprises about 15% to about 60% of the total core weight, preferably about 20% to about 40%, more preferably about 27% to about 33% of the total core weight. The weight ratio of C$_6$ sugar alcohol to saccharide is from about 1:9 to about 9:1, preferably about 1:4 to about 4:1, more preferably about 1:2 to about 2:1, and most preferably from about 0.98:1 to about 1.02:1.

Typical lubricants or glidants for use in the instant delivery system include: calcium stearate, magnesium stearate, light mineral oil, polyethylene glycol, stearic acid, talc, vegetable oil hydrogenated, zinc stearate, sodium stearyl fumarate, silica derivatives and cornstarch, sodium benzoate, sodium chloride, magnesium lauryl sulfate, sodium lauryl sulfate, polyacylethylene monostearate, sterotex, sodium acylate, DL-leucine, sodium oleate, and lauric acid, most preferably magnesium stearate.

The lubricants are typically present from 0.5 to 5%, preferably up to 4%, more preferably up to 3.5%, most preferably about 0.95 to about 2.0%. A highly preferred embodiment contains about 1.0% to about 1.2% of this component.

Preferred wetting agents are surface-active compounds, i.e. surfactants, e.g. anionic surfactants of the alkylsulfate type such as sodium, potassium or magnesium n-dodecylsulfate, n-tetradecylsulfate, n-hexadecylsulfate or n-octadecylsulfate; of the alkyl ether sulfate type, e.g. sodium, potassium or magnesium n-dodecyloxyethyl sulfate, n-tetradecyloxyethyl sulfate, n-hexadecyloxyethyl sulfate or n-octadecyloxyethyl sulfate; or of the alkylsulfonate type e.g. sodium, potassium or magnesium n-dodecanesulfonate, e.g. sodium, potassium or magnesium n-tetradecanesulfonate, n-hexadecanesulfonate or n-octadecanesulfonate.

Further suitable surfactants are nonionic surfactants of the fatty acid polyhydroxy alcohol ester type such as sorbitan monolaurate, sorbitan tristerate or triolate, polyethylene glycol fatty acid ester such as polyoxyethyl sterate, polyethylene glycol 400 sterate, polyethylene glycol 2000 sterate, preferably ethylene oxide/propylene oxide block polymers of the Pluronics ®

(BWC) or Synperonic ® (ICI) type, polyglycerol-fatty acid esters, glyceryl-fatty acid esters, etc.

Especially suitable is sodium lauryl sulfate.

The surfactants (or wetting agents), when present, are preferably present from about 0.2% to about 2%, more preferably from about 0.4% to about 0.75%, still more preferably 0.5% to about 0.6% based on the total weight of the system.

Further excipients are those customarily used in tabletting for the preparation of granulates, e.g. binders, dispersants, and the like. Thus it is possible to use conventional auxiliaries such as starch, e.g. potato starch, corn starch or amylopectin, directly compressible starches, hydrolyzed starches, other cellulose derivatives, dibasic calcium phosphate dihydrate, calcium sulfate dihydrate, acacia, gelatin, polyvinylpyrrolidone (PVP), starch paste, starch pregelatinized, alginates, tragacanth, cellulose, especially microcrystalline cellulose, in addition to the cited excipients.

The core may be made into any desired shape e.g. round, oval, tubular and the like for most finished form, and may also differ in size, depending on the amount to materials used. Furthermore, the core can be transparent, opaque, colorless or colored, so as to impart an individual appearance or immediate identification to the product.

The semipermeable wall surrounds the core and is impermeable to the core components but permeable to water and/or gastro-intestinal fluids. Suitable wall materials for forming the semi-permeable wall are e.g. the polymeric microporous materials described in the literature, e.g. in U.S. Pat. Nos. 3,916,899 and 3,977,404, and which are not metabolized in the gastrointestinal tract, i.e. which are excreted substantially intact. For example, it is possible to use acylated cellulose derivatives (cellulose esters) which are substituted by one to three acetyl groups or by one or two acetyl groups and a further acyl other than acetyl, e.g. cellulose acetate, cellulose triacetate, agar acetate, amylose acetate, cellulose acetate ethyl carbamate, cellulose acetate phthalate, cellulose acetate methyl carbamate, cellulose acetate succinate, cellulose acetate dimethylaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate propionate, cellulose acetate, cellulose acetate diethylaminoacetate, cellulose acetate octate, cellulose acetate laurate, cellulose acetate p-toluenesulfonate, cellulose acetate butyrate, and other cellulose acetate derivatives. Suitable semi-permeable membrane materials are also hydroxypropyl methylcellulose and polymeric epoxides, copolymers of alkylene oxides and alkyl glycidyl ethers, polyglycols or polylactic acid derivatives and further derivatives thereof. It is also possible to use mixtures, e.g. of water insoluble acrylates (e.g. the copolymer of ethyl acrylate and methyl methacrylate).

The wall comprises preferably at least one cellulose acetate, a hydroxy $C_1$-$C_4$alkyl-$C_1$-$C_4$alkyl cellulose, and a poly $C_2$-$C_4$alkylene glycol.

The wall poly $C_2$-$C_4$alkylene glycol is preferably polyethyleneglycol and preferably has an average molecular weight of 8000. It typically comprises about 6% to about 10%, preferably about 8% by weight of the wall material.

The hydroxy $C_1$-$C_4$alkyl $C_1$-$C_4$alkyl cellulose is advantageously a hydroxy $C_1$-$C_4$alkyl methyl cellulose or a hydroxypropyl-$C_1$-$C_4$alkyl cellulose, more preferably hydroxypropyl methyl cellulose.

Most advantageously the hydroxy $C_1$-$C_4$alkyl $C_1$-$C_4$alkyl cellulose has a viscosity in the range of about 10 through about 20 cps, and most preferably about 15 cps. It typically comprises about 6% to about 10%, more preferably 8% of the wall weight.

The cellulose acetate component of the wall is typically two cellulose acetates and comprises about 80%—about 88%, most preferably about 84% of the wall weight. The most advantageous cellulose acetates are cellulose acetate 320S NF and cellulose acetate 398-10 NF with the weight ratio of the 320S:398-10 being about 5:1 to about 8:1, more preferably about 6:1 to about 7:1, still more preferably about 6.5:1 to about 6.75:1, most preferably about 6.62:1 to about 6.64:1.

The drug, polymers, osmotic agents, coloring agents and wetting agents are wet granulated using purified water. The wet granulation is then dried, lubricated, and compressed into tablet cores. The cores are then coated using an organic solvent solution or an agueous dispersion of the coating polymers to obtain a semipermeable coating. Delivery ports are then provided in the semi-permeable membrane coating or the coated tablet has been designed to create a delivery port in situ when placed in the environment of use thereof.

The following Examples are presented to exemplify and do not limit the invention.

| Examples 1-3 | | | |
|---|---|---|---|
| Core | | | |
| 1. Carbamazepine | 100 | 200 | 400 |
| 2. Hydroxypropylmethyl-cellylose 2910, 3 cps USP | 11.75 | 23.5 | 40 |
| 3. Hydroxyethylcellulose 250L NF | 5.0 | 10.0 | 10 |
| 4. Hydroxyethyl cellulose 250H NF | 10.0 | 20.0 | 20 |
| 5. Mannitol USP | 27.25 | 55.15 | 108.5 |
| 6. Dextrates NF | 27.25 | 54.15 | 108.5 |
| 7. Na Lauryl SO$_4$ NF | 1.25 | 2.5 | 5.0 |
| 8. Iron Oxide, Yellow | 0.5 | — | 0.85 |
| 9. Iron Oxide, Red | — | 0.05 | 0.15 |
| 10. Titanium Dioxide USP | — | 0.65 | — |
| 11. Magnesium Stearate NF | 2.0 | 4.0 | 7.0 |
| | 185 | 370 | 700 |
| Semipermeable Wall | | | |
| 12. Cellulose Acetate 320S NF | 16.06 | 18.25 | 14.6 |
| 13. Cellulose Acetate 398-10 NF | 2.42 | 2.75 | 2.2 |
| 14. Hydroxypropylmethyl-cellulose 2910, 15 cps USP | 1.76 | 2.0 | 1.6 |
| 15. Polyethyleneglycol, 8000 NF | 1.76 | 2.0 | 1.6 |
| | 22.0 | 25.0 | 20.0 |

Components 1 through 10 are blended in a planetary or a high shear mixer for 15 minutes. This mixture is then wet granulated using purified water, USP to obtain a suitable consistency. The granulate is then passed through a mill and mesh screen to obtain suitable granules. The granules are dried in a tray or a fluid bed drier. The dried granules are blended with the magnesium stearate for 5 minutes and then passed through a rotary tablet press to obtain cores of suitable strength. Separately components 12 to 15 are dissolved in a mixture of 80 parts methylene chloride and 20 parts methanol. This solution is then used to coat the cores produced above via fluid bed coater or a pan coater. A delivery portal is provided by drilling a hole through the coating into the core using a mechanical or laser drilling device.

We claim:

1. An oral osmotic dosage delivery form adapted to deliver carbamazepine comprising
   (a) core comprising
      i. carbamazepine in an amount sufficient to deliver an effective amount thereof over the intended delivery time;
      ii. an effective amount of a crystal habit modifier for said carbamazepine selected from the group consisting of $C_{1-4}$alkyl cellulose, hydroxypropyl cellulose, hydroxypropyl-$C_{1-4}$alkyl cellulose, sodium carboxymethyl cellulose, sodium carboxymethyl-$C_{1-4}$alkylcellulose, and gelatin;
      iii. from about 2% to about 15% of the total core weight of a mixture of at least two different hydroxy-$C_1$-$C_4$alkyl celluloses which may be hydroxyalkyl celluloses having different alkyl groups or hydroxyalkyl celluloses having the same alkyl groups but are of different grades, wherein the ratio of the higher viscosity hydroxy-$C_1$-$C_4$alkyl cellulose to the lower viscosity hydroxy-$C_1$-$C_4$alkyl cellulose is about 2:1;
      iv. a $C_6$ sugar alcohol;
      v. a mono- or di-saccharide;
      vi. from 0 to an effective amount of a tabletting lubricant; and
      vii. from 0 to an effective amount of a wetting agent;
         said $C_6$ sugar alcohol and said mono- or di-saccharide together comprising from about 15% to about 60% of the core total weight and the weight ratio of the $C_6$ sugar alcohol to said mono- or di saccharide is from about 1:9 to about 9:1;
   (b) a semi-permeable wall around said core permeable to water or gastric fluid; and
   (c) a hole through said semipermeable wall connecting said core with the external environment.

2. The delivery form of claim 1 wherein said active agent is present in an amount of from about 100 mg to about 400 mg, based on carbamazepine free base.

3. The delivery form of claim 1 wherein said crystal habit modifier is hydroxypropyl cellulose, said crystal habit modifier being present in an amount of about 9% to about 15% by weight based upon the amount said carbamazepine as free base.

4. The delivery form of claim 1 wherein said hydroxy-$C_1$-$C_4$alkyl celluloses are selected from different grades of the same hydroxy-$C_1$-$C_4$alkyl cellulose.

5. The delivery form of claim 4 wherein said hydroxy-$C_1$-$C_4$alkyl celluloses are selected from hydroxyethylcelluloses.

6. The delivery form of claim 5 wherein said hydroxyethyl cellulose grades are selected from 250H, 250L, 250J, 250E, 250G, 250K, 250M, 250MH, 250H4, and 250HH.

7. The delivery form of claim 1 wherein said $C_6$ sugar alcohol is selected from mannitol, sorbitol and galactitol.

8. The delivery form of claim 7 wherein said $C_6$ sugar alcohol is mannitol.

9. The delivery form of claim 1 wherein said mono- or di-saccharide is selected from glyceraldehyde, threose, erythrose, lyxose, xylose, arabinose, ribose, talose, galactose, idose, gulose, mannose, glucose, altrose, xylulose, tagatose, sorbose, psicose, hamamalose, allose, their corresponding ketoses and deoxy forms, pseudoheptulose, maltose, lactose, sucrose, cellobiose, isomaltose, and mixtures thereof.

10. The delivery form of claim 9 wherein said mono- or di-saccharide is dextrates N.F.

11. The delivery form of claim 1 wherein said tableting lubricant is magnesium stearate.

12. The delivery form of claim 1 wherein said wetting agent is sodium lauryl sulfate.

13. The delivery form of claim 1 further comprising a pharmaceutically acceptable coloring agent which is present in said core.

14. The delivery form of claim 1 wherein said semipermeable wall comprises at least one cellulose acetate, hydroxy-$C_1$-$C_4$alkyl, $C_1$-$C_4$alkyl cellulose, and a poly $C_2$-$C_4$ alkylene glycol.

15. The delivery form of claim 14 wherein said poly$C_2$-$C_4$alkyleneglycol is polyethyleneglycol 8000.

16. The delivery form of claim 14 wherein said poly$C_2$-$C_4$alkyleneglycol is present in an amount of from about 6% to about 10% based on the total permeable wall weight.

17. The delivery form of claim 14 wherein said hydroxy-$C_1$-$C_4$alkyl $C_1$-$C_4$alkyl cellulose is present in an amount of from about 6% to 10% based on the total semipermeable wall weight.

18. The delivery form of claim 14 wherein said hydroxy-$C_1$-$C_4$alkyl $C_1$-$C_4$alkyl cellulose in said semipermeable wall is hydroxypropylmethyl cellulose.

19. The delivery form of claim 14 wherein said hydroxy-$C_1$-$C_4$alkyl $C_1$-$C_4$alkyl cellulose is a grade thereof having a viscosity of about 10-20 cps 20. The delivery form of claim 14 wherein said semipermeable wall comprises at least two different cellulose acetates.

21. The delivery form of claim 20 wherein said cellulose acetates are cellulose acetate 320S NF and cellulose acetate 398-10 NF and the radio of cellulose acetate 320S NF: cellulose acetate 398-10 NF is from about 5:1 to about 8:1.

22. The delivery form of claim 20 wherein the ratio of cellulose acetate 320S NF: cellulose acetate 398-10 NF is from about 6.62:1 to about 6.64:1.

23. The delivery form of claim 1 comprising
   (a) a core of

| | |
|---|---|
| carbamazepine | 100–400 mg |
| hydroxypropylmethyl cellulose | 10–45 mg |
| hydroxyethyl cellulose 250L | 5–10 mg |
| hydroxyethyl cellulose 250H | 2.5–20 mg |
| Mannitol | 25–110 mg |
| Dextrates NF | 25–110 mg |
| Sodium Lauryl Sulfate | 1–7 mg |
| Magnesium Stearate | 1–8 mg |
| Coloring agents | 0.5–1.0 mg | in which the hydroxyethyl cellulose 250L:hydroxyethyl cellulose 250H ratio is from 1:4 to 4; and
   (b) a semipermeable wall of

| | |
|---|---|
| cellulose acetates | 15–20 mg |
| hydroxypropylmethyl cellulose | 1.5–2.0 mg |
| polyethyleneglycol 8000 | 1.5–2.0 mg | and
   (c) a hole through said semipermeable wall connecting said core and the external environment.

* * * * *